(12) United States Patent
Livneh

(10) Patent No.: US 7,632,270 B2
(45) Date of Patent: Dec. 15, 2009

(54) MULTI-MODE SURGICAL INSTRUMENT

(75) Inventor: Steve Livneh, Amherstburg (CA)

(73) Assignee: Bovie Medical Corporation, Petersburg, FL (US)

( * ) Notice: Subject to any disclaimer, the term of this patent is extended or adjusted under 35 U.S.C. 154(b) by 941 days.

(21) Appl. No.: 11/042,818

(22) Filed: Jan. 25, 2005

(65) Prior Publication Data

US 2005/0165443 A1 Jul. 28, 2005

Related U.S. Application Data

(60) Provisional application No. 60/539,459, filed on Jan. 26, 2004.

(51) Int. Cl.
*A61B 18/18* (2006.01)
*A61B 17/28* (2006.01)

(52) U.S. Cl. ..................... 606/51; 606/205

(58) Field of Classification Search ........... 606/45–52, 606/205–207
See application file for complete search history.

(56) References Cited

U.S. PATENT DOCUMENTS

| | | | |
|---|---|---|---|
| 5,282,800 A | 2/1994 | Foshee et al. | |
| 5,830,231 A | 11/1998 | Geiges, Jr. | |
| 5,913,874 A * | 6/1999 | Berns et al. | 606/205 |
| 5,935,126 A * | 8/1999 | Riza | 606/51 |
| 6,494,877 B2 * | 12/2002 | Odell et al. | 606/1 |
| 6,540,695 B1 * | 4/2003 | Burbank et al. | 600/564 |
| 2002/0068879 A1 * | 6/2002 | Lubock et al. | 600/567 |

* cited by examiner

*Primary Examiner*—Michael Peffley
(74) *Attorney, Agent, or Firm*—Howard & Howard Attorneys PLLC

(57) ABSTRACT

A surgical instrument for performing surgical procedures includes a handle assembly and a power supply. The handle assembly is configured to accept a variety of surgical cartridges, each having a pair of clamping or cutting members, for clamping animal anatomy. Electrical power is supplied to the clamping or cutting members for perform electrosurgery.

31 Claims, 14 Drawing Sheets

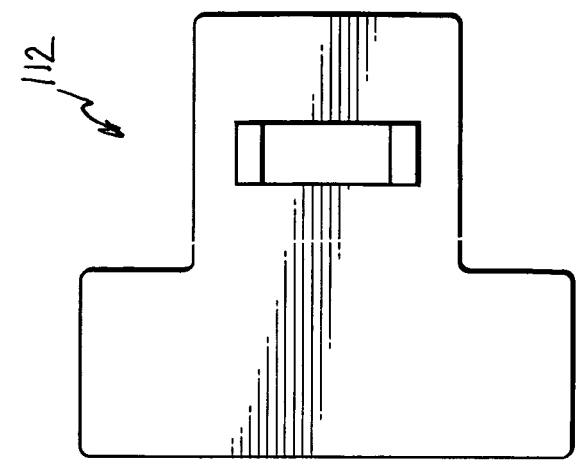
FIG - 23
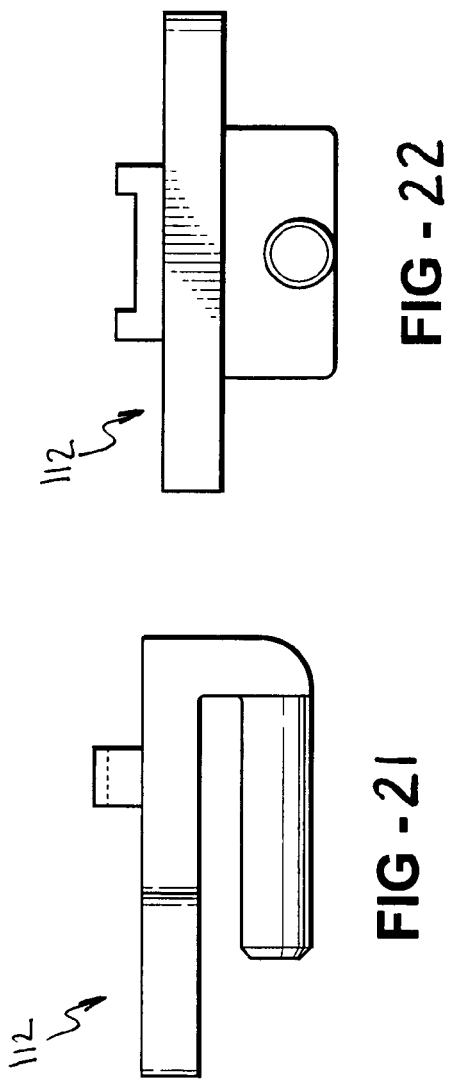
FIG - 22
FIG - 21
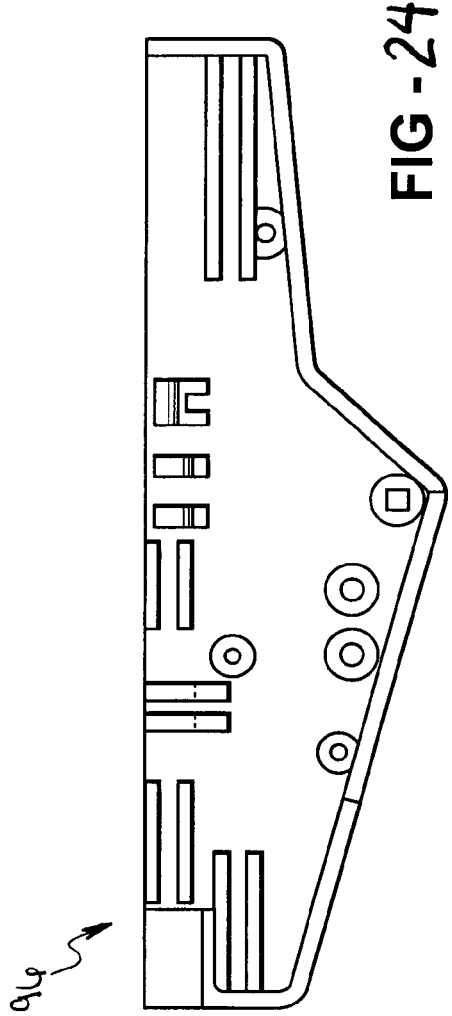
FIG - 24

MULTI-MODE SURGICAL INSTRUMENT

CROSS REFERENCE TO RELATED APPLICATION

This application claims the benefit of provisional application Ser. No. 60/539,459, filed Jan. 26, 2004.

BACKGROUND OF THE INVENTION

1. Field of the Invention

The invention relates generally to the field of surgical instruments for use in performing minimally invasive surgical procedures.

2. Description of the Prior Art

Endoscopic surgery relies on scopes and miniature video cameras which enable the visualization of internal organs via miniature incisions. This provides the surgeon with a clear picture either on a video screen above the operating table or on a head held video screen. The surgeon then executes operative measures of tissues and organs (i.e., moving, cutting, coagulating, manipulating, etc.) while operating an array of endoscopic surgical hand instruments that are inserted via similar small incisions and being viewed, during the operation, through the scope or video camera.

Today's endoscopic surgical instruments may be divided into three categories: intended life and usage; electro-surgical instruments; and inert instruments. By intended life and usage, the instruments can be a single use instrument that is disposable, a multi-use instrument that is reusable, or a reposable instrument that is semi-disposable. In the reposable instrument, the instrument is intended to be reusable, but crucial elements such as tip inserts, blades, and insulation may be replaced.

The electro-surgical instruments are those where the instrument may provide electro-cautery performance together with mechanical performance such as cutting with scissors and dissecting with dissectors. The sub-categories for the electro-surgical instruments are monopolar instruments, bipolar instruments and DC instruments. A monopolar instrument includes a positive lead that sends current to the patient to cut or cauterize the anatomy of the patient's body that the monopolar instrument contacts. The current exits the patient though a ground in contact with the patient's body. In a bipolar instrument, a positive lead and a negative lead each contact the patient's anatomy. The positive lead sends current to the patient and the negative lead returns the power back to the power supply, through the instrument. The anatomy is cut or cauterized in the selected area of the anatomy between the positive and negative leads. In a DC current instrument, similarly a positive and a negative lead are used to cut or cauterize the selected area of the anatomy between the positive and negative leads.

Based on the above, it is easy to relate to today's realities of the operating room where a large inventory of specific instruments must be kept in an inventory at a high cost. Even the management and maintenance of this inventory is costly and complex. Disposable instruments are a direct added cost to each surgery, while maintaining the reusable and reposable instruments necessitates trained personnel and dedicated sterilization facilities and capabilities.

SUMMARY OF THE INVENTION AND ADVANTAGES

The present inventions provide multi-mode surgical instruments each comprising a handle assembly for being held by medical personnel and a source of electrical power. The handle assembly includes a primary actuator and a docking station. The primary actuator is creates motion to move a pair of clamping members to clamp animal anatomy. The docking station receives any one of various cartridges, each of which supports a pair of such clamping members. The docking station presents a first electrical contact, a first interface and a second interface. The first electrical contact transmits electrical power from the source of electrical power through a first cartridge to a first pair of clamping members. The first interface transmits motion from the actuator to the first pair of clamping members. The second interface transmits motion from the actuator to a second pair of clamping members of a second cartridge.

By incorporating at least two types of interfaces that are triggered by the same actuator, more that one type of cartridge can be within the docking station of the surgical instrument. Therefore, the ability to use more than one type of cartridge, with the same handle, each with a different type of interface, provides flexibility for surgery and inventory maintenance. Additionally, by providing the handle assembly with the actuator and the electrical contacts, if the surgical cartridge is intended to be disposable, material that is ultimately disposed can be minimized.

BRIEF DESCRIPTION OF THE DRAWINGS

Other advantages of the present inventions will be readily appreciated, as the same becomes better understood by reference to the following detailed description when considered in connection with the accompanying drawings wherein:

FIG. 21 is a side view of a reactor for the handle assembly;

FIG. 22 is a front view of the reactor of FIG. 21 for the handle assembly;

FIG. 23 is a top view of the reactor of FIGS. 21 and 22 for the handle assembly;

FIG. 24 is an interior side view of one-half of the housing for the handle assembly.

DETAILED DESCRIPTION OF THE PREFERRED EMBODIMENT

Figure 1:
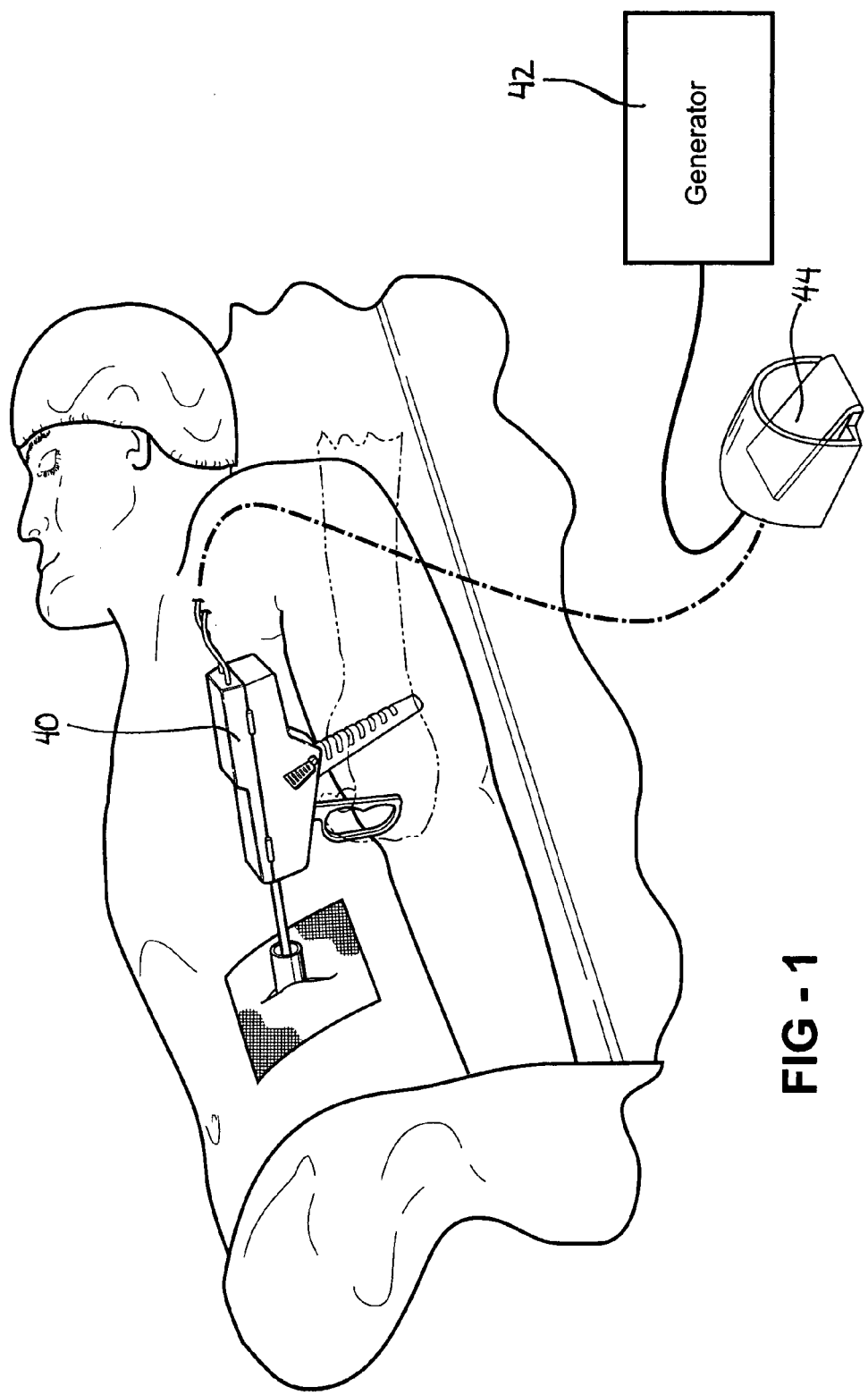
FIG. 1 is a perspective view of the surgical instrument of the subject inventions being used in a surgical environment.
Figure 2:
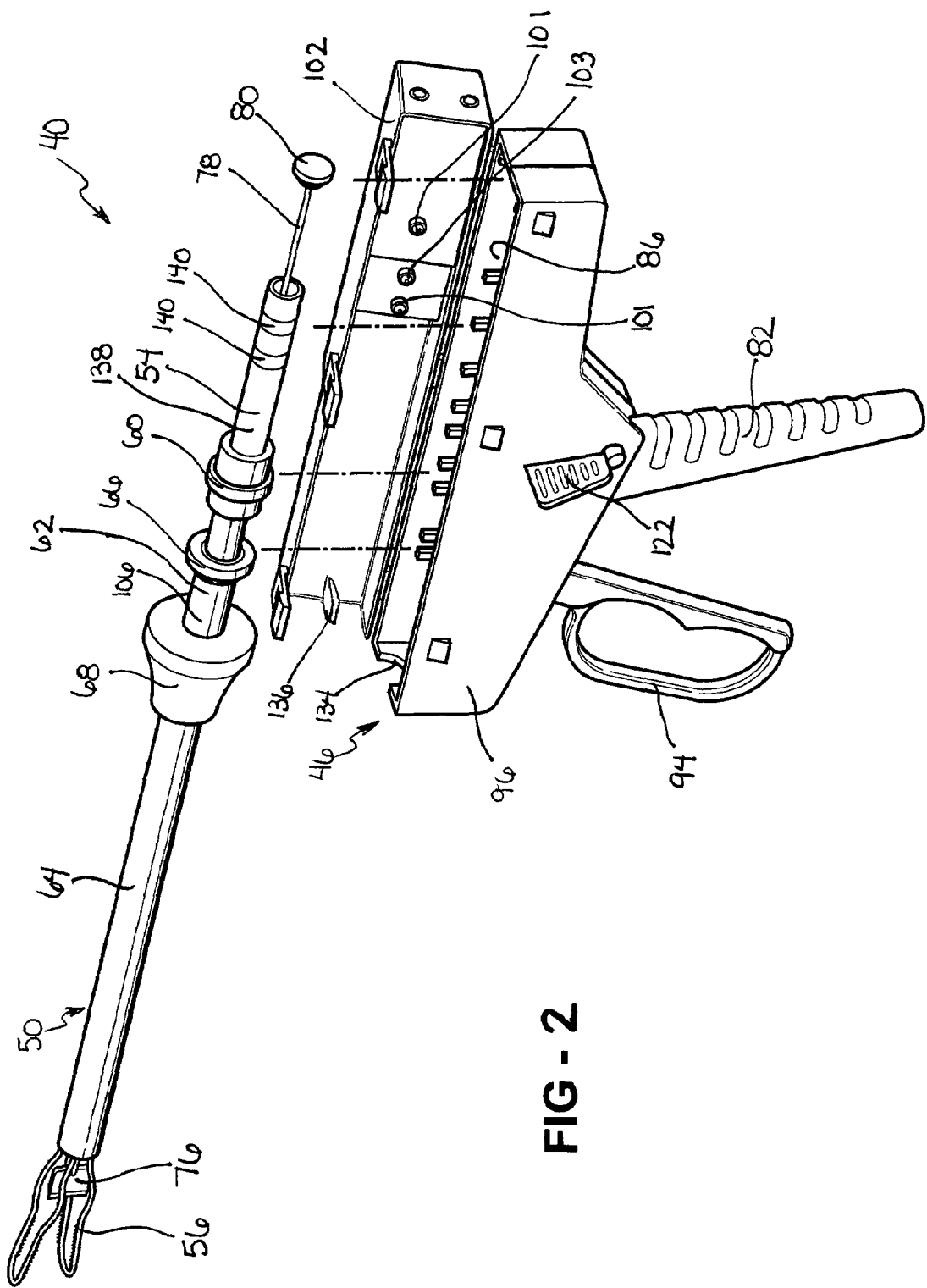
FIG. 2 is an exploded perspective view of the handle assembly and a bipolar surgical cartridge with a dissecting blade.
Figure 3:
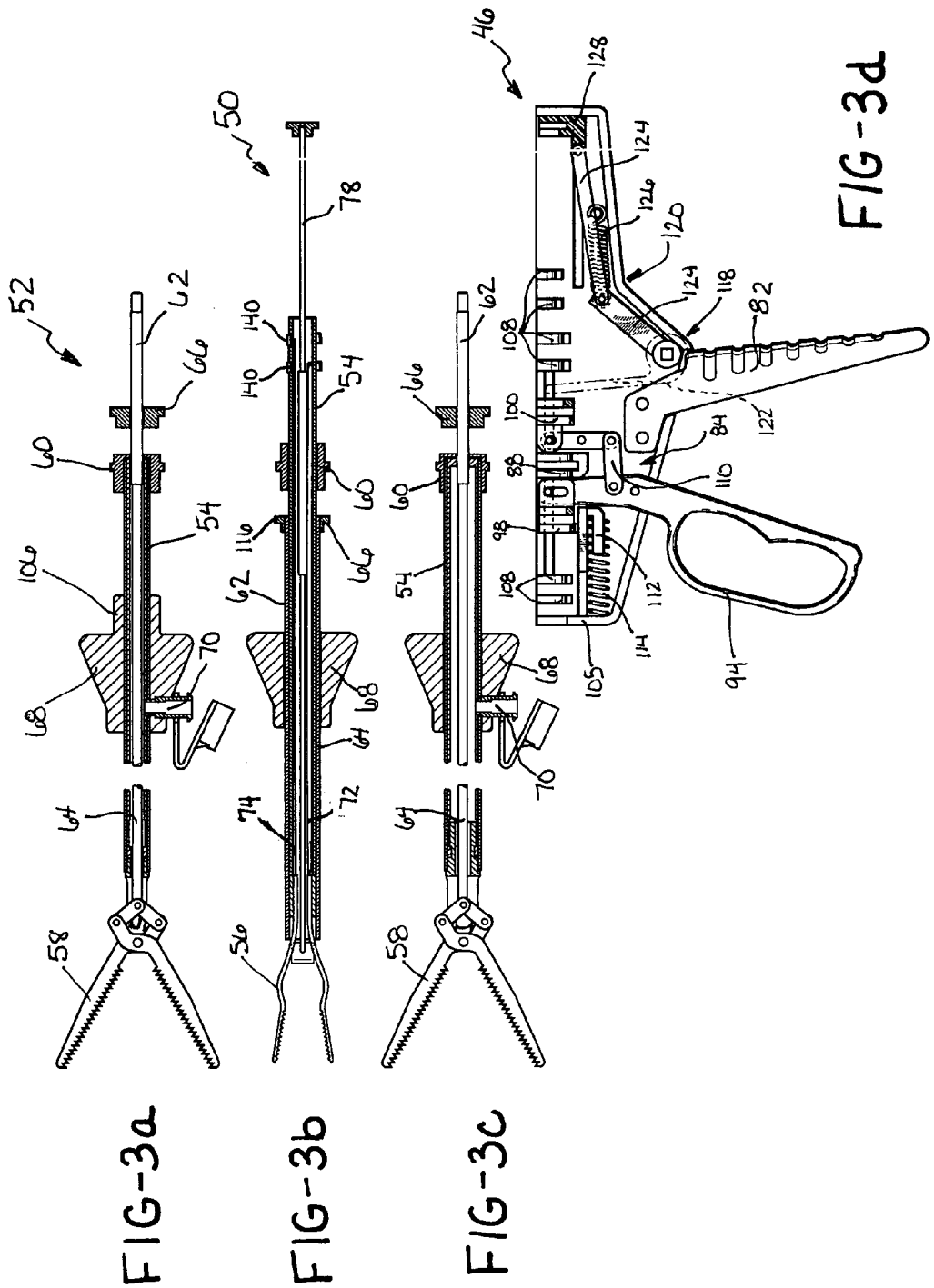
FIG. 3a is a partial cross-sectional view of a monopolar surgical cartridge for use in the surgical instrument.
FIG. 3b is a partial cross-sectional view of a bipolar surgical cartridge for use in the surgical instrument.
FIG. 3c is a partial cross-sectional view of a monopolar surgical cartridge for use in the surgical instrument.
FIG. 3d is a partial cross-sectional side view of a handle assembly for use with the surgical instrument.
Figure 4:
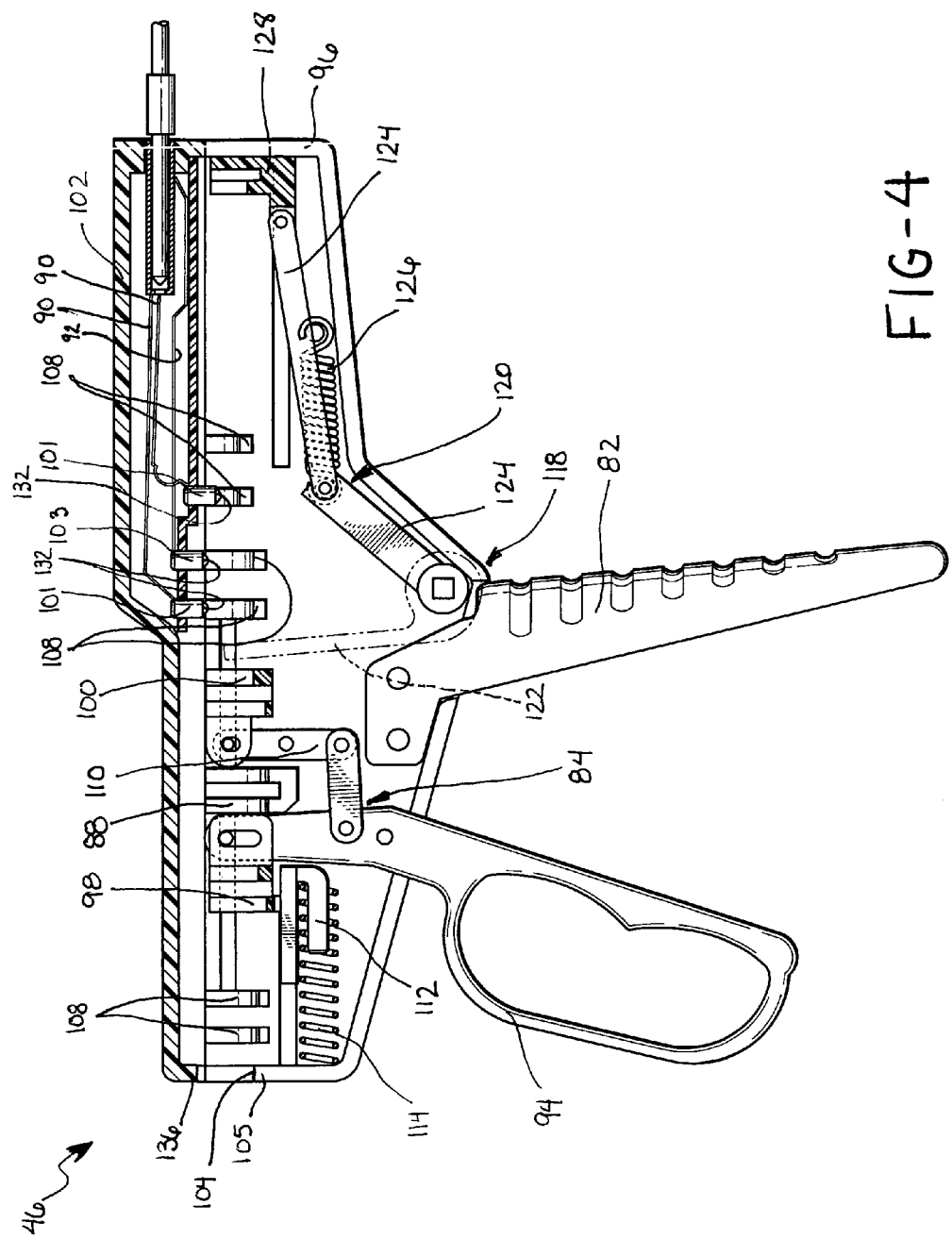
FIG. 4 is a partial cross-sectional side view of a handle assembly with the trigger relaxed.
Figure 5:
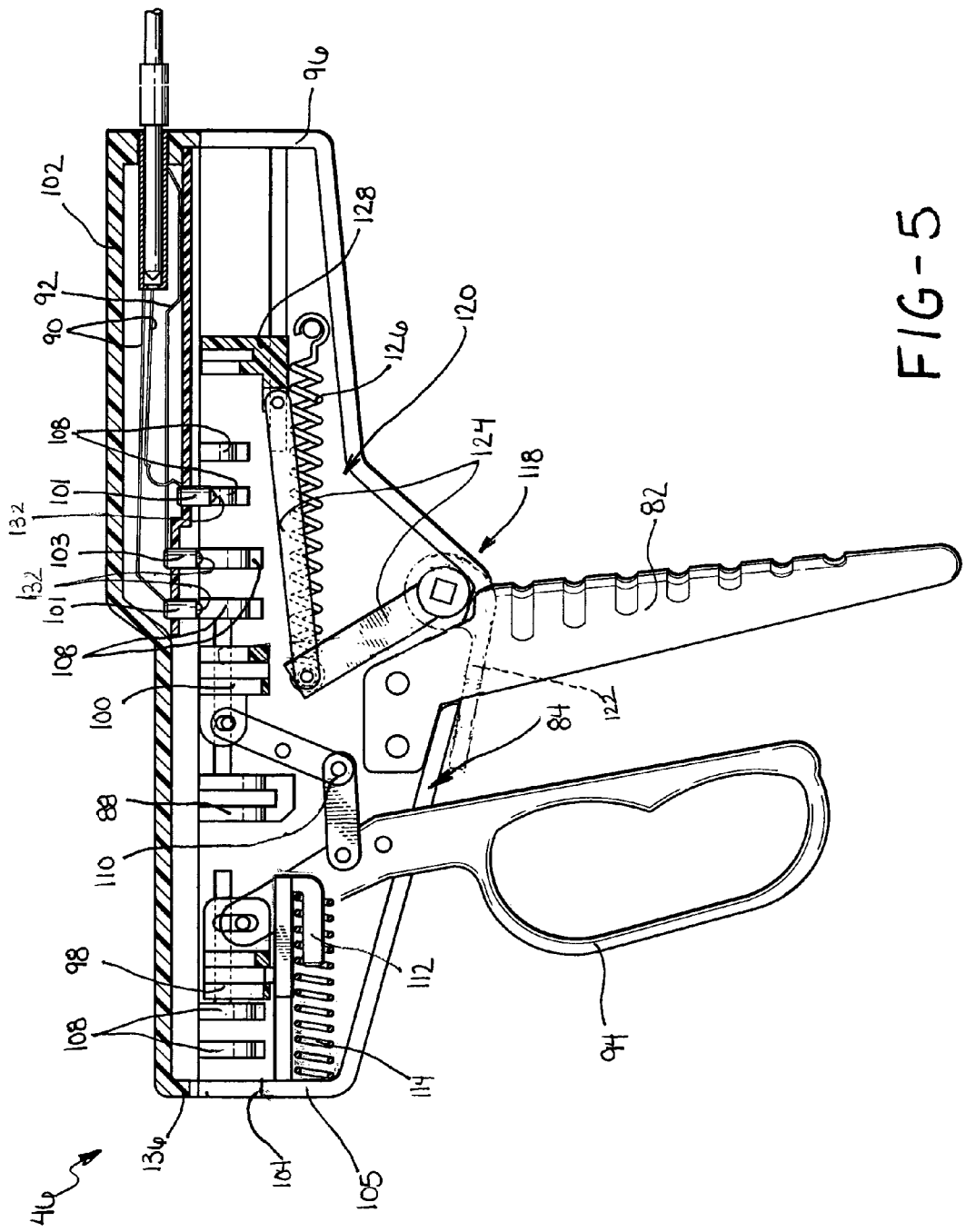
FIG. 5 is a partial cross-sectional side view of a handle assembly with the trigger pulled toward the grip.

Referring to the Figures, wherein like numerals indicate like parts throughout the several views, a multi-mode surgical instrument for performing electro-surgical procedures is shown at 40. The surgical instrument 40 performs various cutting and cauterizing procedures on animal anatomy, primarily with the use of electrical current. Animal anatomy can include, but is not limited to tissue, muscles, blood vessels and tendons of humans or animals. The electrical current can be monopolar, bipolar or DC and is provided by connection of the surgical instrument 40 to a power supply 42, as shown in FIG. 1. It is preferable, for safety reasons, that the current is only supplied from the power supply 42 to the surgical instrument 40 when a switch, such as a foot pedal 44, is depressed by medical personnel operating the surgical instrument 40.

The surgical instrument 40 includes a handle assembly 46 for being held by medical personnel, and a source of electrical power 48. The handle assembly 46 receives various types of surgical cartridges 50, 52 that are either bipolar 50 or monopolar 52. However, it will be appreciated that other types of surgical cartridges 50, 52 are also possible, such as a DC surgical cartridge.

Each type of surgical cartridge 50, 52 is rotatably supported in the handle assembly 46 and comprises a casing 54, a pair of clamping members 56, 58, an anchor 60, a transmission 62 and at least one electrical lead 72, 74. The casing 54, which is tubular, extends to a distal end of the handle assembly 46. The anchor 60, which is a radial ring 140, is disposed on the casing 54 and prevents relative longitudinal movement between the casing 54 and the handle assembly 46 when the ring 140 is engaged with the handle assembly 46. The clamping members 56, 58 can be of any shape to facilitate clamping the anatomy, such as tongs 56 or clamps 58. However, the clamping members 56, 58 are not limited to tongs 56 and clamps 58, but can also be scissors or probes. Additionally, the type of clamping members 56, 58 are not limited by the type of power or current supplied to the surgical cartridge 50, 52. Therefore, it will be appreciated that a bipolar cartridge can incorporate clamps 58 or any other type of clamping member. Similarly, the monopolar surgical cartridge can incorporate tongs 56 or any other type of clamping member.

The transmission 62 includes a shaft 64 that is movably supported by the casing 54 and connected to a disk 66 at one end and to the clamping members 56, 58 at the other end. The disk 66 extends radially from the shaft 64 and is movable rectilinearly relative to the casing 54 when engaged with the handle assembly 46. The shaft 64 surrounds and is slidably 102 supported about, or slidably 102 disposed within, the tubular casing 54 to transmit rectilinear motion relative to the casing 54 to open or close the pair of clamping members 56, 58.

A rotary dial 68 can encircle the casing 54 or the transmission 62 to allow rotation of the cartridge 50, 52 within the handle assembly 46. Additionally, a port 70, for flushing and sterilizing the inside of the surgical cartridge 50, 52, can be formed through the dial 68 and the casing 54. Alternatively, if the surgical cartridge 50, 52 does not have a dial 68, the port 70 can be formed through the casing 54 only.

A first electrical lead 72 is disposed in the casing 54 for a monopolar surgical cartridge 52. For a bipolar surgical cartridge 50, a first and a second electrical lead 72, 74 are disposed in the casing 54.

Figure 7:
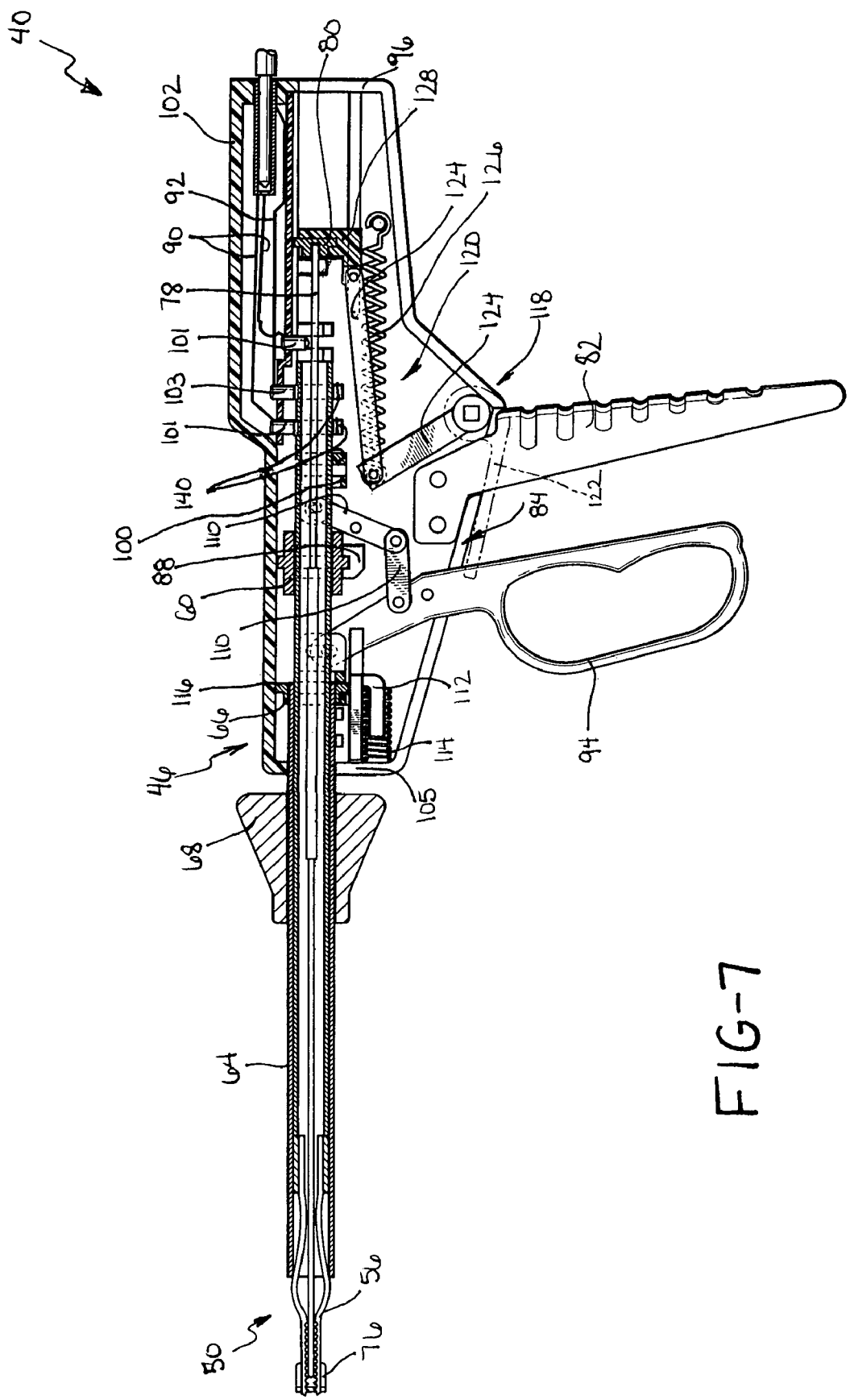
FIG. 7 is a partial cross-sectional side view of a surgical instrument having a bipolar surgical cartridge inserted into the handle assembly with the clamping members in the closed position and the dissecting blade in the extended position.
Figure 8:
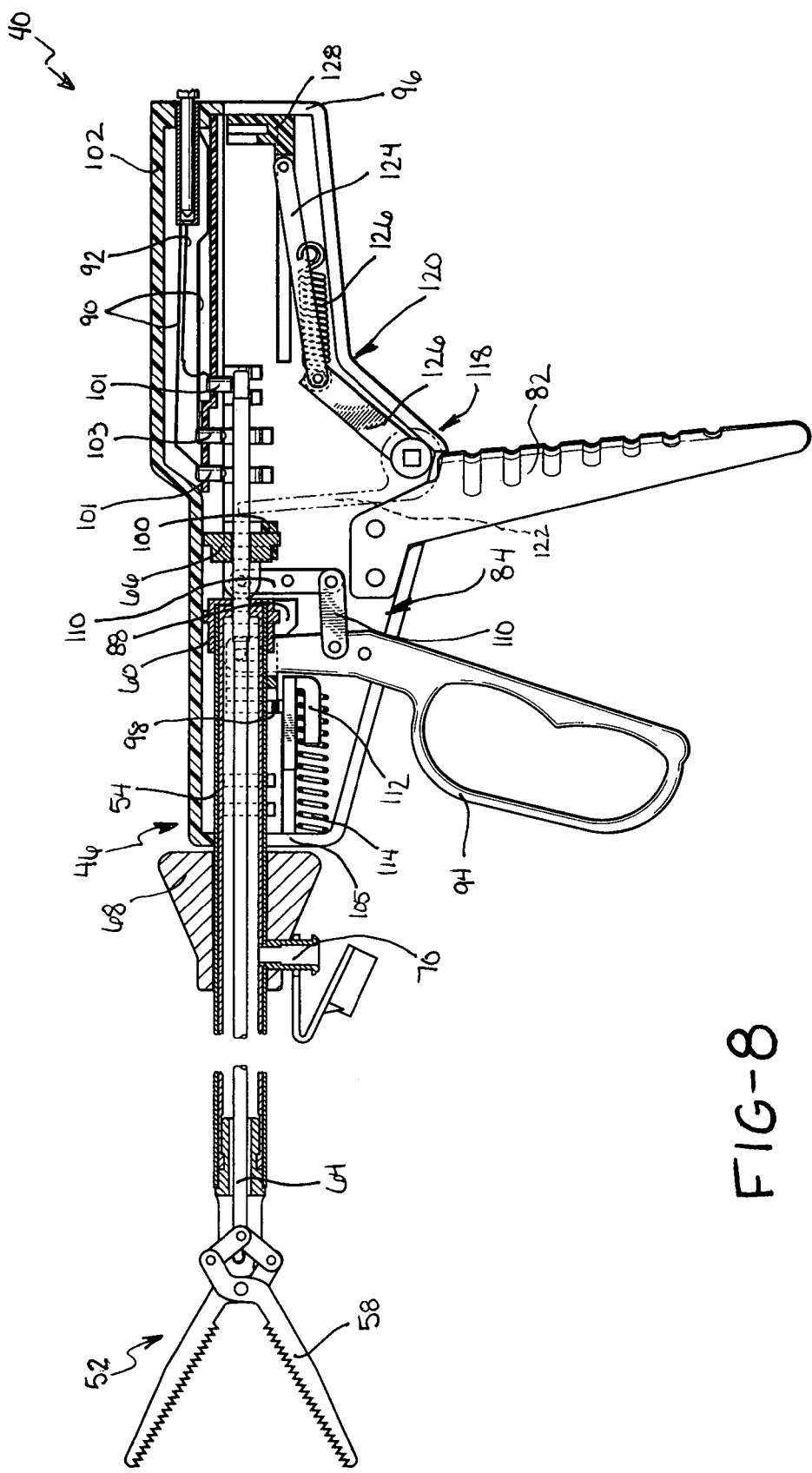
FIG. 8 is a partial cross-sectional side view a surgical instrument having a monopolar surgical cartridge inserted into the handle assembly with the clamping members in the open position.
Figure 9:
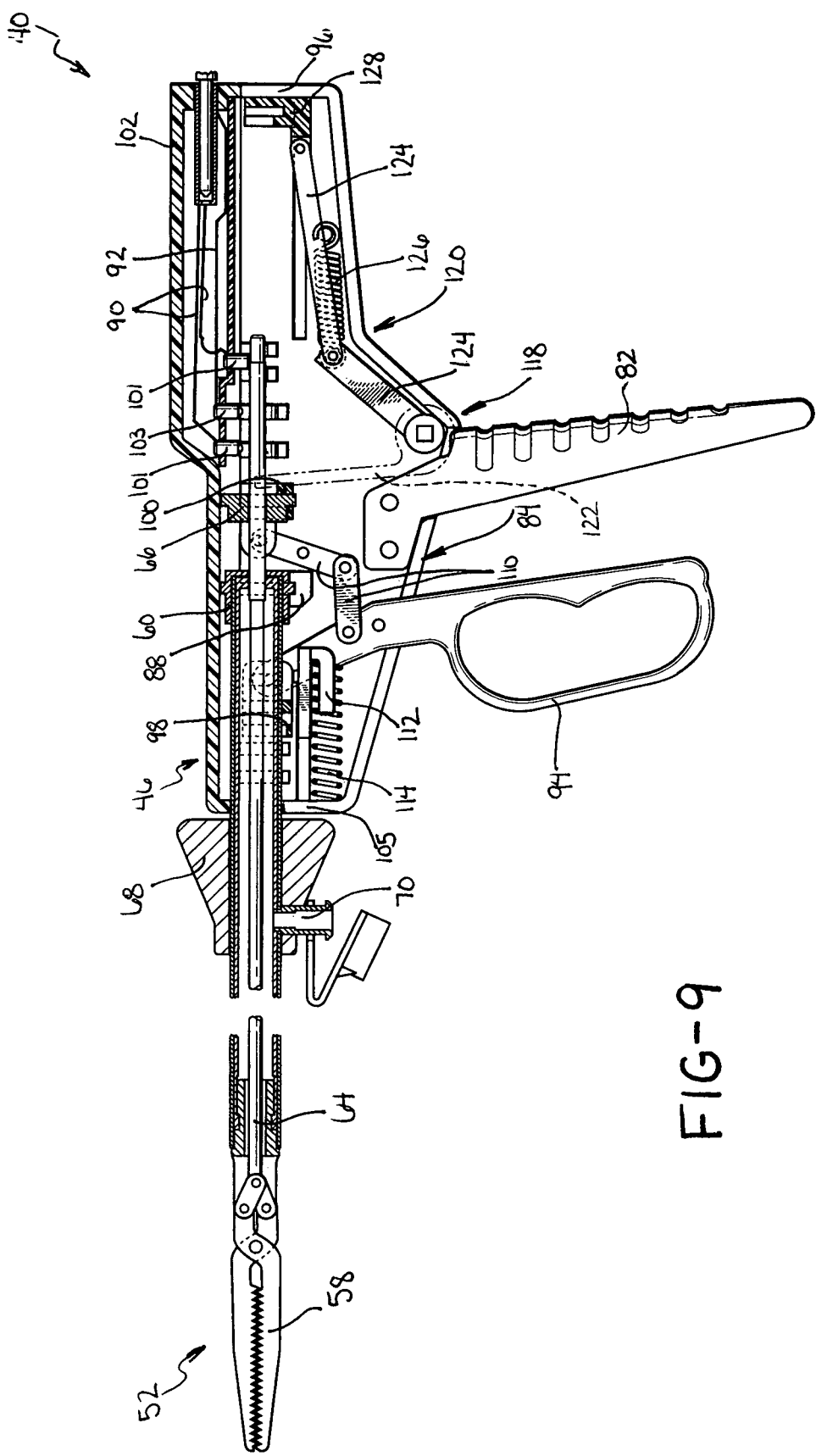
FIG. 9 is a partial cross-sectional side view of a surgical instrument having a monopolar surgical cartridge inserted into the handle assembly with the clamping members in the closed position.
Figure 10:
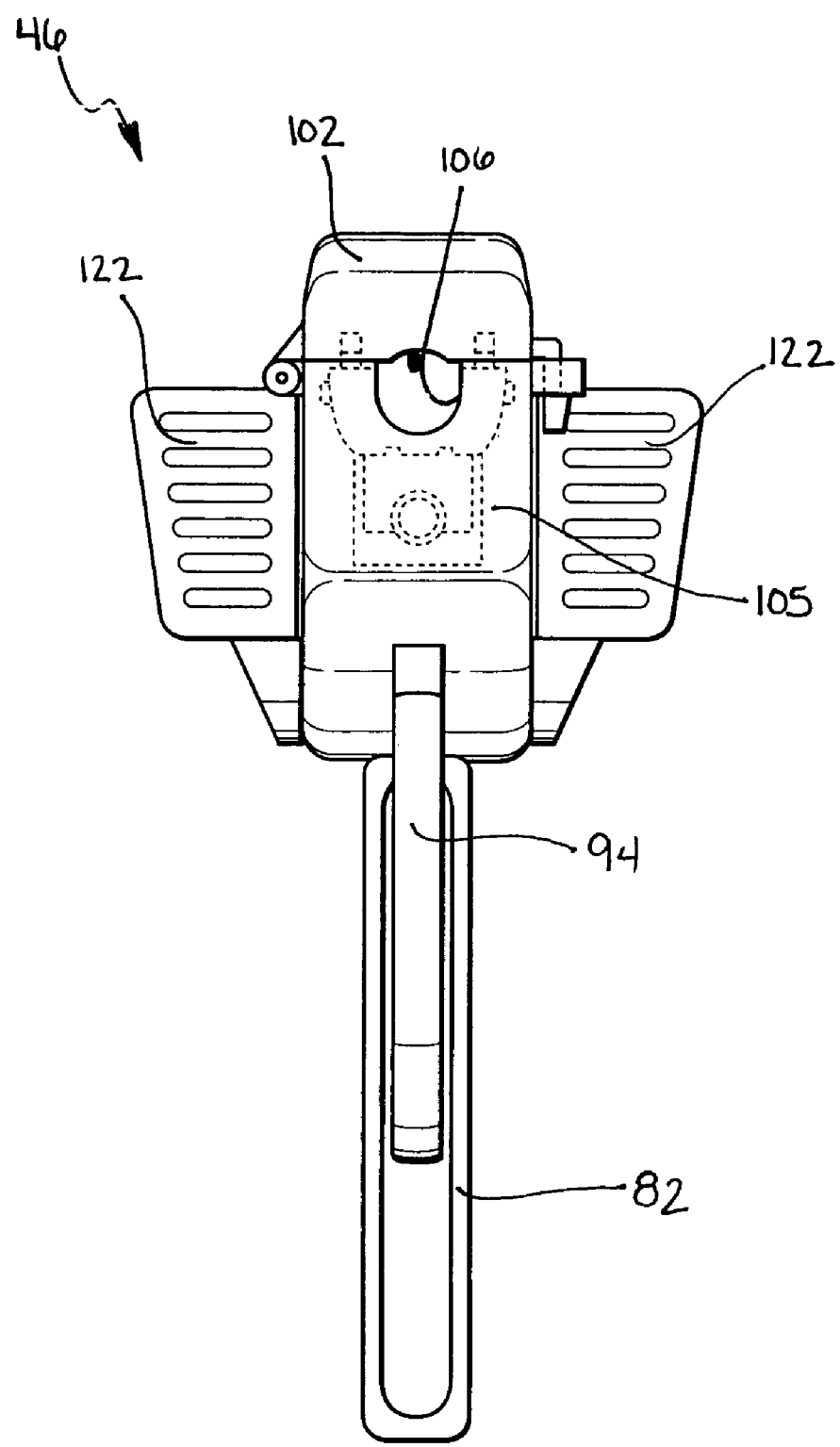
FIG. 10 is a front view of the handle assembly with no cartridge inserted in the handle.
Figure 11:
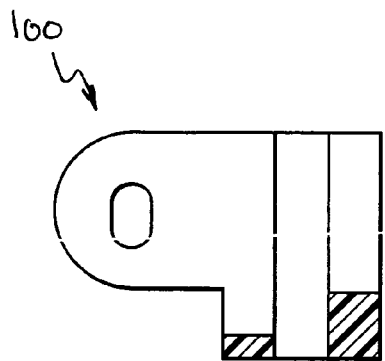
FIG. 11 is a side view partially in section of a second interface for the handle assembly.
Figure 12:
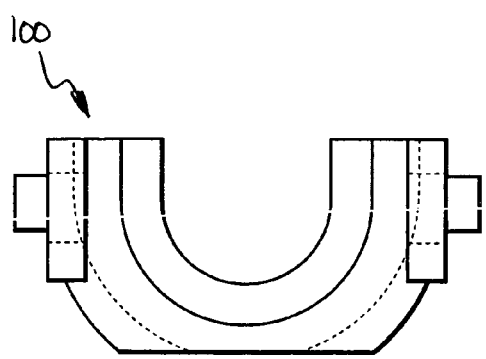
FIG. 12 is a front view of the second interface of FIG. 11 for the handle assembly.
Figure 13:
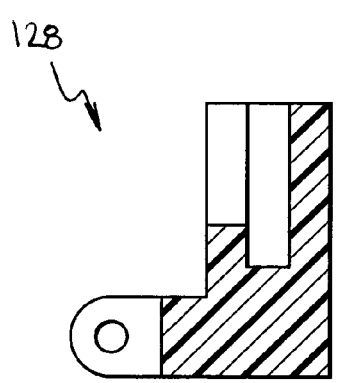
FIG. 13 is a side view partially in section of a seat for the biasing device of the handle assembly.
Figure 14:
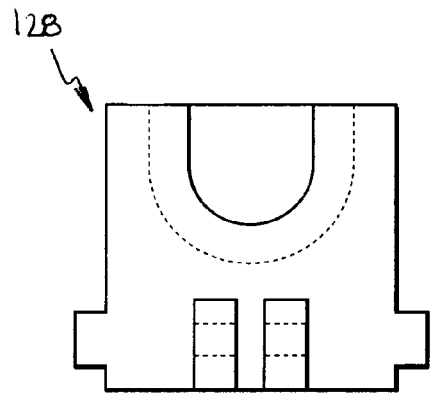
FIG. 14 is a front view of the seat of FIG. 13 for the biasing device of the handle assembly.
Figure 15:
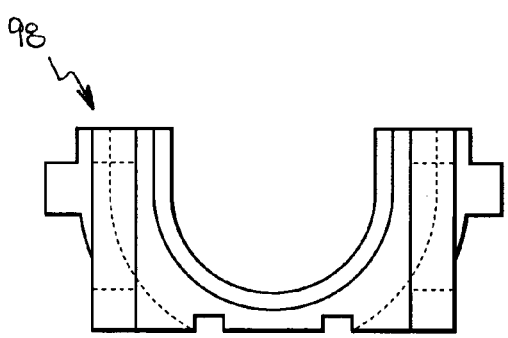
FIG. 15 is a front view of a first interface for the handle assembly.
Figure 16:
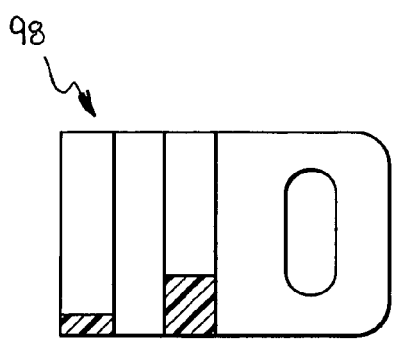
FIG. 16 is a cross-sectional side view of the first interface of FIG. 15 for the handle assembly.
Figure 20:
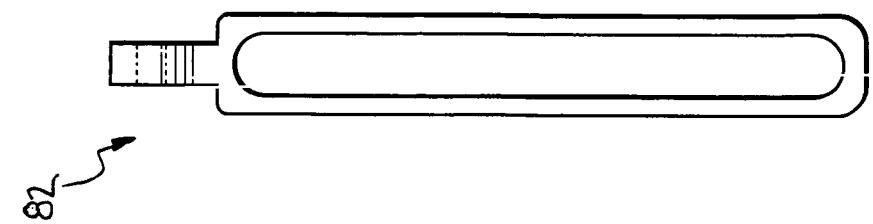
FIG. 20 is a front view of the grip of FIG. 19 for the handle assembly.
Figure 19:
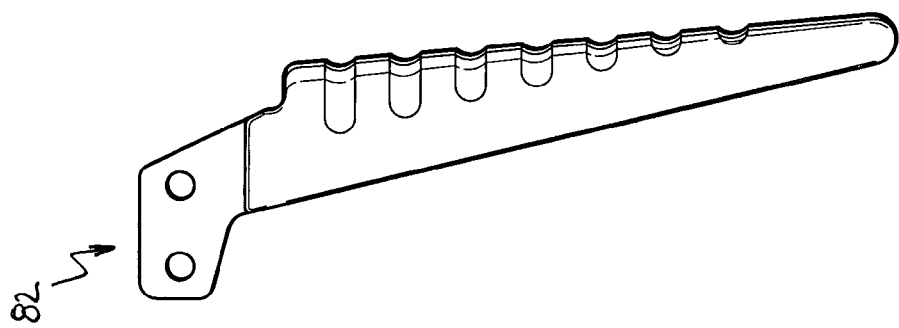
FIG. 19 is a side view of a grip for the handle assembly.
Figure 18:
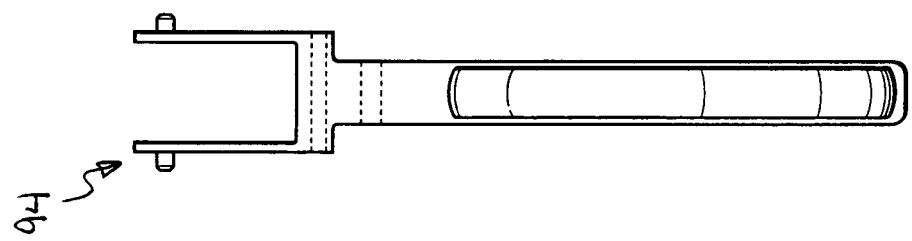
FIG. 18 front view of the trigger of FIG. 17 for the handle assembly.
Figure 17:
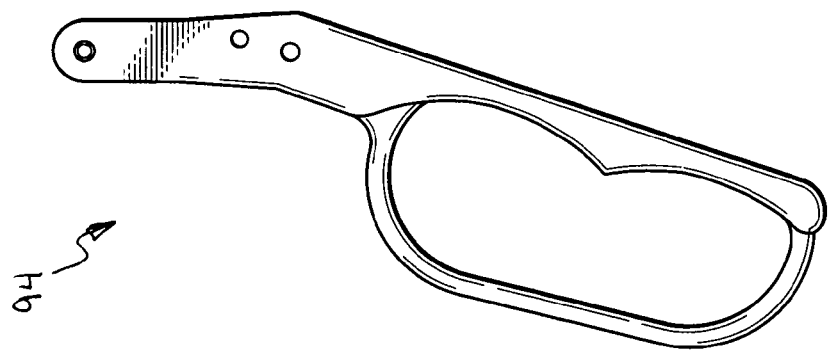
FIG. 17 is a side view of a trigger for the handle assembly.
Figure 25:
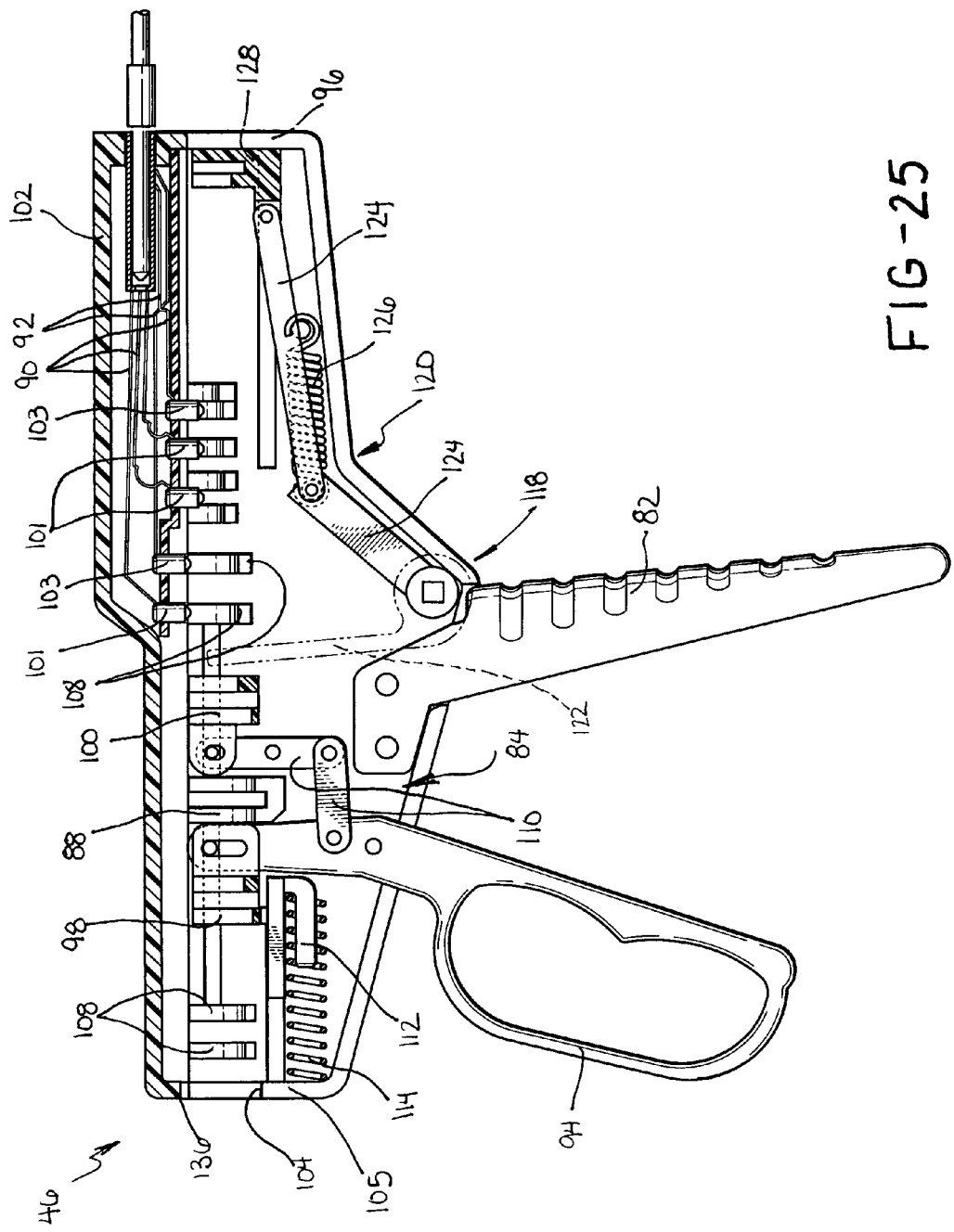
FIG. 25 is a partial cross-sectional side view of a handle assembly for use with a surgical cartridge having a lid and five electrical contacts, including contacts for DC instrumentation.

Additionally, the surgical cartridge 50 can also include a dissecting blade 76. In this configuration, a stem 78 is supported within the tubular casing 54 for rectilinear movement between a retracted position, as shown in FIG. 7, and an extended position, as shown in FIG. 8, between a pair of clamping members 56. The stem 78 extends from the tubular casing 54 and a fitting 80 extends radially from the stem 78 for actuation when engaged with the handle assembly 46. The dissecting blade 76 can extend from an end of the stem 78 to perform dissection during operation of the surgical instrument 40. Although the use of the stem 78 and the dissecting blade 76 is illustrated with the bipolar surgical cartridge 50, it should be appreciated that the dissecting blade 76 is not limited to this configuration and can be used with other types of surgical cartridges.

The handle assembly 46 includes a grip 82, a primary actuator 84, a docking station 86, a saddle 88, and electrical connectors 90, 92. The grip 82 is for being gripped by medical personnel. The primary actuator 84 includes a trigger 94 for being moved relative to, and in reaction to, holding the grip 82 and for creating motion to move a pair of clamping members 56, 58 to clamp the anatomy.

The docking station 86 is provided to receive any one of various cartridges 50, 52. The docking station 86 presents a housing 96, a first and a second interface 98, 100, electrical contacts 101, 103 and a lid 102. The docking station 86 has a front wall 105 that defines a collar 104 of a fixed diameter. More specifically, the collar 104 is between the housing 96 and the lid 102. Each surgical cartridge 50, 52 has a cylindrical neck 106 with a diameter equal to the diameter of the collar 104 of the docking station 86. Therefore, when a surgical cartridge 50, 52 is inserted into the docking station 86, the neck 106 of the surgical cartridge 50, 52 is rotatably supported by the neck 106.

When a surgical cartridge 50, 52 is inserted into the docking station 86, the anchor 60 is inserted into the saddle 88 to prevent relative movement between the anchor 60 and the handle assembly 46. The saddle 88 is semicircular to allow radial rotation of the anchor 60 within the saddle 88. The first and the second interfaces 98, 100 are for receiving the disk 66 of the transmission 62 and are positioned on each side of the saddle 88, within the housing 96. Similar to the saddle 88, each interface 98, 100 has a semicircular profile to not only receive the disk 66, but to allow radial rotation of the disk 66 within the interface 98, 100. If the surgical cartridge 50, 52 is a monopolar surgical cartridge 52, for example, the disk 66 can be inserted into the second interface 100. When a bipolar surgical cartridge 50 is inserted into the docking station 86, the disk 66 can inserted into the first interface 98. To provide additional structure for the surgical cartridges 50, 52, a plurality of supports 108 are formed in the housing 96. Each support 108 has a semicircular profile to cradle the transmission 62 and/or the casing 54 and allow radial rotation.

The trigger 94 of the primary actuator 84 is connected to the first and the second interfaces 98, 100. The trigger 94 is operatively connected to the first interface 98 to transmit motion from the primary actuator 84 to a pair of clamping members 56, 58. Linkage 110 connects the trigger 94 to the second interface 100 to transmit motion from the primary actuator 84 to a pair of clamping members 56, 58 when a surgical cartridge 50, 52 is received in the docking station 86. When the trigger 94 is pulled toward the grip 82, the first and the second interfaces 98, 100 slide rectilinearly away from the saddle 88 in opposite directions.

Additionally, a reactor 112 is disposed in the housing 96 of the docking station 86 to resist motion moving the clamping members 56, 58 when a disk 66 of a surgical cartridge 50 is disposed in engagement with the first interface 98. The reactor 112 includes a compression spring 114 that reacts against the front wall 105 of the housing 96. When the disk 66 of the transmission 62 of the bipolar surgical cartridge 50 is disposed in the first interface 97, a radial brim 116 that extends from the disk 66 engages the reactor 112. Therefore, when the trigger 94 is pulled toward the grip 82, the reactor 112 reacts against the front wall 105 of the housing 96, creating a "spring-loaded" feel when the trigger 94 is actuated. By virtue of the brim 116 being radial, the disk 66 of the bipolar surgical cartridge 50 remains in engagement with the reactor 112 even if the bipolar surgical cartridge 50 is rotated within the handle assembly 46. When the disk 66 of the transmission 62 of the monopolar surgical cartridge 52 is disposed in the second interface 100, the reactor 112 is not engaged.

Figure 6:
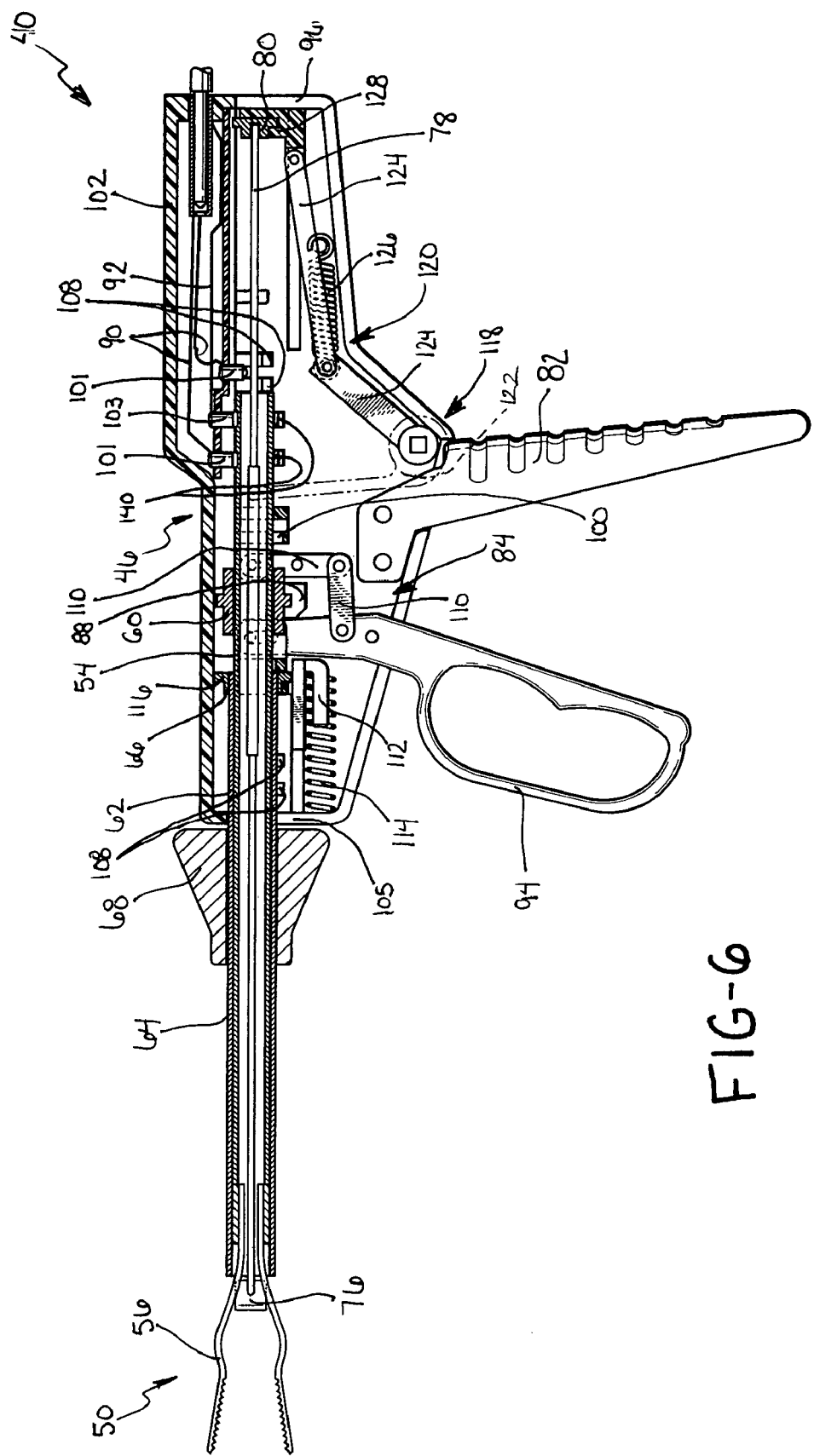
FIG. 6 is a partial cross-sectional side view of a surgical instrument having a bipolar surgical cartridge inserted into the handle assembly with the clamping members in the open position and the dissecting blade in the retracted position.

The housing 96 of the docking station 86 also includes an additional actuator 118 and a biasing device 120. The additional actuator 118 includes a lever 122 pivotally supported adjacent the grip 82. In order to provide a surgical instrument 40 that is conducive to use with the left or the right hand, the lever 122 is supported on both sides of the grip 82. The additional actuator 118 creates motion, in response to pivoting the lever 122, to move the stem 78 that is supported for rectilinear movement between a retracted position, as shown in FIG. 6, and an extended position, as shown in FIG. 7, between the clamping members 56. The biasing device 120 includes a coupling 124, an extension spring 126 and a seat 128. The coupling 124 connects the lever 122 and the seat 128. The seat 128 receives the fitting 80 from the stem 78. When the lever 122 is rotated, the additional actuator 118 and the stem 78 slide rectilinearly in the direction of the lever 122 rotation. The extension spring 126 connects the coupling 124 to the docking station 86 to bias the additional actuator 118 and the stem 78 to the retracted position when the lever 122 is released.

The docking station 86 includes a lid 102 that is movable between an open position for receiving a cartridge 50, 52 within the housing 96 and a closed position for retaining the cartridge 50, 52 within the housing 96. The lid 102 includes a first electrical connector 90 for receiving a first type of electrical power and for transmitting the first type of electrical power to the first electrical contact 101 and a second electrical connector 92 for receiving a second type of electrical power and for transmitting the second type of electrical power to the second electrical contact 103. The electrical contacts 101, 103 are supported on the lid 102 and include a plunger device 132, such as a ball plunger, biased into engagement with the cartridge 50, 52 when a cartridge 50, 52 is in the docking station 86 and the lid 102 is closed. However, it can be appreciated that other types of contacts 101, 103 can be used so long they maintain constant contact with the cartridge 50, 52 when the cartridge 50, 52 is rotated within the docking station 86.

Additionally, the housing 96 defines a semi-circular opening 134 on the front wall of the docking station 86. A rib 136 depends from the lid 102, near the front wall 105 of the docking station 86. When the lid 102 is in the closed position, the semi-circular opening 134 and the rib 136 cooperate to define the collar 104 for supporting the neck 106 of the surgical cartridge 50, 52. When the surgical cartridge 50, 52 is inserted into the docking station 86 and the lid 102 is in the closed position, the rib 136 is tangential to the neck 106 to provide rotational support to the surgical cartridge 50, 52. It can be appreciated, however, that other types of support for the cartridge 50, 52 can also be used.

The electrical contacts 101, 103 are supported on the lid 102. The first electrical contact 101 is for transmitting electrical power from the power source through a surgical cartridge 50, 52 to a pair of clamping members 56, 58. The second electrical contact 103 is for transmitting electrical power from the pair of clamping members 56, 58 to the power source. Preferably, the surgical instrument 40 is configured to have electrical contacts 101, 103 that support bipolar and monopolar surgery. Accordingly, the handle assembly 46 can provide two first electrical contacts 101 and a single second electrical contact 103. When a bipolar surgical cartridge 50 is inserted into the docking station 86, the cartridge 50 contacts one of each of the first and the second electrical contacts 101, 103. Likewise, when a monopolar surgical cartridge 52 is inserted into the docking station 86, the cartridge 52 contacts only the first electrical contact 101. Insulation 138 is disposed on portions of the surgical cartridge 50, 52 to prevent unwanted contact between the electrical leads 72, 74 of the surgical cartridge 50, 52 and other components enclosed in the docking station 86. For example, in the bipolar surgical cartridge 50, the casing 54 is a multilumen extrusion which has a vinyl extrusion surrounding and insulating the electrical leads 72, 74.

When a monopolar surgical cartridge 52 is inserted into the docking station 86, the first electrical lead 72 contacts the first electrical contact 101 for electrical engagement. The first electrical lead 72 receives power from the first electrical contact 101 and extends to the pair of clamping members 56, 58 to conduct electrical power through anatomy when the anatomy is disposed between the pair of clamping members 58.

When the bipolar surgical cartridge 50 is inserted into the docking station 86, the first and the second electrical leads 72, 74 contact the first and the second electrical contacts 101, 103, respectively, for electrical engagement. The first electrical lead 72 receives power from the first electrical contact 101 and extends to the clamping members 56. The second electrical lead 74 sends power from the clamping members 56 to the second electrical contact 101. Therefore, the leads 72, 74 extend to a pair of clamping members 56 for conducting electrical power through anatomy when the anatomy is disposed between the pair of clamping members 56.

On the bipolar surgical cartridge 50, for example, each of the first electrical leads 72 can include a corresponding ring 140, surrounding the casing 54, for maintaining engagement with the first electrical contact 101 during rotation of the casing 54 in the docking station 86. Additionally, the diameter of the ring 140 can be larger than the diameter of the casing 54 to allow the clamping members 56, the casing 54 and/or the transmission 62 of the surgical instrument 40 to be whatever diameter is desired to perform the surgery. For example, the instrument can accommodate a surgical instrument 40 with up to a 10 mm diameter. If a surgical instrument 40 with a 5 mm diameter is inserted into the docking station 86, the diameter of the ring 140 would still be 10 mm to allow continuous contact with the electrical contacts 101, 103. Additionally, the neck 106 would also be of a 10 mm diameter to ensure the surgical cartridge 50, 52 is retained securely in the docking station 86. If the neck 106 surrounds the transmission 62, which moves rectilinearly in response to actuation of the actuator, the neck 106 would have a length sufficient to remain within the collar 104 during the rectilinear travel of the transmission 62 and the collar 104.

Many modifications and variations of the present invention are possible in light of the above teachings. In addition, the reference numerals in the claims are merely for convenience and are not to be read in any way as limiting.

The invention claimed is:

1. A multi-mode surgical instrument (40) comprising;
a handle assembly (46) for being held by medical personnel, and
a source of electrical power (42) on said handle assembly, said handle assembly (46) including a primary actuator (84) for creating motion to move a pair of clamping members (56), (58) to clamp animal anatomy, and
said handle assembly (46) including a docking station (86) for receiving any one of various cartridges (50), (52) each of which supports a pair of such clamping members (56), (58) with said docking station (86) presenting a first electrical contact (101) for transmitting electrical power from said source (42) through a first cartridge (50), (52) to a first pair of clamping members (56), (58) and a first interface (98) for transmitting motion from said actuator (84) to the first pair of clamping members (56), (58) and a second interface (100), different from said first interface (98), for transmitting motion from said actuator (84) to a second pair of clamping members (56), (58) of a second cartridge (50), (52), different from said first pair of clamping members (56), (58) of said first cartridge (50), (52).

2. An instrument (40) as set forth in claim 1 including a first cartridge (50), (52) disposed in said docking station (86) and movably supporting a first pair of clamping members (56), (58), said first cartridge (50), (52) having a first electrical lead (72) in electrical engagement with said first electrical contact (101) in said docking station (86) and extending to said first pair of clamping members (56), (58) for conducting electrical power through anatomy disposed between said first pair of clamping members (56), (58), said first cartridge (50), (52) including a first transmission (62) for transmitting motion from said first interface (98) to said first pair of clamping members (56), (58).

3. An instrument (40) as set forth in claim 2 wherein said first cartridge (50), (52) includes a stem (78) supported for rectilinear movement between a retracted position and an extended position between said first clamping members (56), (58) and said handle assembly (46) includes an additional actuator (118) for creating motion to move said stem (78).

4. An instrument (40) as set forth in claim 3 wherein said handle assembly (46) includes a biasing device (120) for biasing said additional actuator (118) and the stem (78) to the retracted position.

5. An instrument (40) as set forth in claim 2 including a second cartridge (50), (52) for disposition in said docking station (86) and movably supporting a second pair of clamping members (56), (58).

6. An instrument (40) as set forth in claim 5 wherein said second interface (100) includes a second transmission (62) for transmitting motion from said second interface (100) to said second pair of clamping members (56), (58).

7. An instrument (40) as set forth in claim 6 wherein said docking station (86) presents a second electrical contact (103) and said second cartridge (50), (52) includes a first electrical lead (74) in electrical engagement with said second electrical contact (103) in said station (86) and extending to said second pair of clamping members (56), (58) for conducting electrical power through anatomy disposed between said second pair of clamping members (56), (58).

8. An instrument (40) as set forth in claim 1 wherein said docking station (86) presents a second electrical contact (103) for transmitting electrical power from said source (48) to a second cartridge (50), (52).

9. An instrument (40) as set forth in claim 8 wherein said handle assembly (46) includes a first electrical connector (90) for receiving a first type of electrical power and for transmitting said first type of electrical power to said first electrical contact (101) and a second electrical connector (92) for receiving a second type of electrical power and for transmitting said second type of electrical power to said second electrical contact (103).

10. An instrument (40) as set forth in claim 9 wherein said handle assembly (46) includes a grip (82) for being gripped, said primary actuator (84) includes a trigger (94) for being moved relative to said grip (82) and in reaction to holding the grip (82), said trigger (94) being operatively connected to said first interface (98).

11. An instrument (40) as set forth in claim 10 wherein said second interface (100) includes linkage (110) connecting said trigger (94) to said second interface (100) for moving said second interface (100) in response to movement of said trigger (94).

12. An instrument (40) as set forth in claim 10 wherein said handle assembly (46) includes an additional actuator (118) for creating motion to move a stem (78) supported for rectilinear movement between a retracted position and an extended position between the first clamping members (56), (58), said additional actuator (118) including a lever (122) pivotally supported adjacent said grip (82).

13. An instrument (40) as set forth in claim 12 wherein said handle assembly (46) includes a biasing device (120) for biasing said lever (122) and the stem (78) to the retracted position.

14. An instrument (40) as set forth in claim 1 wherein said handle assembly (46) includes a saddle for receiving an anchor of a cartridge for preventing relative movement between such an anchor and said handle assembly.

15. An instrument (40) as set forth in claim 14 wherein said handle assembly (46) includes an additional actuator (118) for creating motion to move a stem (78) supported for rectilinear movement between a retracted position and an extended position between the first clamping members (56), (58).

16. An instrument (40) as set forth in claim 15 wherein said handle assembly (46) includes a biasing device (120) for biasing said additional actuator (118) and the stem (78) to the retracted position.

17. An instrument (40) as set forth in claim 16 wherein said docking station (86) presents a second electrical contact (103) for transmitting electrical power from said source (48) to a second cartridge (50), (52).

18. An instrument (40) as set forth in claim 14 wherein said handle assembly (46) includes a reactor (112) operable to resist motion moving the clamping members (56), (58) of one of the first cartridge (50), (52) and the second cartridge (50), (52) only in response to one of the first cartridge (50), (52) and the second cartridge (50), (52) being disposed in engagement with one of said first interface (98) and said second interface (100).

19. An instrument (40) as set forth in claim 18 wherein said handle assembly (46) includes a first electrical connector (90) for receiving a first type of electrical power and for transmitting said first type of electrical power to said first electrical contact (101) and a second electrical connector (92) for receiving a second type of electrical power and for transmitting said second type of electrical power to said second electrical contact (103).

20. An instrument (40) as set forth in claim 1 wherein said docking station (86) includes a lid (102) movable between an open position for receiving a cartridge (50), (52) and a closed position enclosing the cartridge (50), (52).

21. An instrument (40) as set forth in claim 20 wherein said first electrical contact (101) is supported on said lid (102).

22. An instrument (40) as set forth in claim 21 wherein said first electrical contact (101) includes a plunger device (132) biased into engagement with the cartridge (50), (52).

23. An instrument (40) as set forth in claim 21 wherein said lid (102) presents a second electrical contact (103) for transmitting electrical power to a second cartridge (50), (52).

24. An instrument (40) as set forth in claim 23 wherein said lid (102) includes a first electrical connector (90) for receiving a first type of electrical power and for transmitting said first type of electrical power to said first electrical contact (101) and a second electrical connector (92) for receiving a second type of electrical power and for transmitting said second type of electrical power to said second electrical contact (103).

25. A multi-mode surgical instrument (40) comprising;
a handle assembly (46) for being held by medical personnel and including a primary actuator (84) for creating motion to clamp animal anatomy,
a source of electrical power (42) on said handle assembly, and
a first cartridge (50), (52) movably supporting a first pair of clamping members (56), (58) and having a first electrical lead (72) extending to said clamping members (56), (58) and a first transmission (62) for transmitting motion to said first pair of clamping members (56), (58), wherein
said handle assembly (46) including a docking station (86) for removably supporting said cartridge (50), (52) and presenting a first electrical contact (101) biased toward said electrical lead (72) for transmitting electrical power from said source (48) to said electrical lead (72) in said cartridge (50), (52) and an interface for transmitting motion from said actuator (84) to said first transmission (62) in said cartridge (50), (52), and
said docking station (86) including a lid (102) movable between an open position for receiving a cartridge (50), (52) and a closed position for retaining the cartridge (50), (52), and
said first electrical contact (101) is supported on said lid (102) and includes a plunger device (132) biased into engagement with the cartridge (50), (52) when said lid is in said closed position.

26. An instrument (40) as set forth in claim 25 wherein said handle assembly (46) includes a saddle (88) for receiving an anchor (60) of said cartridge (50), (52) for preventing relative movement between such an anchor (60) and said handle assembly.

27. An instrument (40) as set forth in claim 26 wherein said first cartridge (50), (52) includes a stem (78) supported for rectilinear movement between a retracted position and an extended position between said first clamping members (56), (58) and said handle assembly (46) includes an additional actuator (118) for creating motion to move said stem (78).

28. An instrument (40) as set forth in claim 27 wherein said handle assembly (46) includes a biasing device (120) for biasing said additional actuator (118) and the stem (78) to the retracted position.

29. An instrument (40) as set forth in claim 26 wherein said first cartridge (50), (52) is rotatably supported in said docking station (86).

30. A multi-mode surgical instrument (40) comprising;
a handle assembly (46) for being held by medical personnel, and
a source of electrical power (42) on said handle assembly,
said handle assembly (46) including a primary actuator (84) for creating motion to move a pair of clamping members (56), (58) to clamp animal anatomy, and
said handle assembly (46) including a docking station (86) for receiving any one of various cartridges (50), (52) each of which supports a pair of such clamping members (56), (58) with said docking station (86) presenting an electrical contact (101) for transmitting electrical power from said source (42) through a first cartridge (50), (52) to a first pair of clamping members (56), (58) and a first interface (98) for transmitting motion from said actuator (84) to the first pair of clamping members (56), (58) and a second interface (100) for transmitting motion from said actuator (84) to a second pair of clamping members (56), (58) of a second cartridge (50), (52),
said handle assembly (46) including a saddle (88) for receiving an anchor (60) of a cartridge (50), (52) for preventing relative movement between such an anchor (60) and said handle assembly (46), and
said handle assembly (46) including a reactor (112) operable to resist motion moving the clamping members (56), (58) of one of the first cartridge (50), (52) and the second cartridge (50), (52) only in response to one of the first cartridge (50), (52) and the second cartridge (50), (52) being disposed in engagement with one of said first interface (98) and said second interface (100).

31. A multi-mode surgical instrument (40) comprising;
a handle assembly (46) for being held by medical personnel, and
a source of electrical power (42) on said handle assembly,
said handle assembly (46) including a primary actuator (84) for creating motion to move a pair of clamping members (56), (58) to clamp animal anatomy, and
said handle assembly (46) including a docking station (86) for receiving any one of various cartridges (50), (52) each of which supports a pair of such clamping members (56), (58) with said docking station (86) presenting an electrical contact (101) for transmitting electrical power from said source (42) through a first cartridge (50), (52) to a first pair of clamping members (56), (58) and a first interface (98) for transmitting motion from said actuator (84) to the first pair of clamping members (56), (58) and a second interface (100) for transmitting motion from said actuator (84) to a second pair of clamping members (56), (58) of a second cartridge (50), (52), said docking station (86) including a lid (102) movable between an open position for receiving a cartridge (50), (52) and a closed position enclosing the cartridge (50), (52), said first electrical contact (101) is supported on said lid (102) and including a plunger device (132) biased into engagement with the cartridge (50), (52).

* * * * *

UNITED STATES PATENT AND TRADEMARK OFFICE
CERTIFICATE OF CORRECTION

PATENT NO. : 7,632,270 B2
APPLICATION NO. : 11/042818
DATED : December 15, 2009
INVENTOR(S) : Steve Livneh It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1360 days.

Signed and Sealed this

Second Day of November, 2010

David J. Kappos
*Director of the United States Patent and Trademark Office*